United States Patent [19]
Bransome

[11] Patent Number: 6,144,508
[45] Date of Patent: Nov. 7, 2000

[54] SELF-VIEWING DEVICE FOR EYES

[76] Inventor: Robert Bransome, 1432 10th St., Lake Park, Fla. 33404-2037

[21] Appl. No.: 09/314,747

[22] Filed: May 19, 1999

[51] Int. Cl.⁷ .................................. G02B 7/02; A61B 3/02
[52] U.S. Cl. ............................................ 359/819; 351/223
[58] Field of Search .................... 359/630, 819; 351/223

[56] References Cited

U.S. PATENT DOCUMENTS

| | | | |
|---|---|---|---|
| 3,787,112 | 1/1974 | Lyons | 351/223 |
| 3,903,870 | 9/1975 | Berndt | 351/223 |
| 4,464,015 | 8/1984 | Shafer | 359/472 |
| 4,902,124 | 2/1990 | Roy, Sr. et al. | 351/223 |
| 5,434,630 | 7/1995 | Bransome | 351/162 |

*Primary Examiner*—Ricky Mack
*Attorney, Agent, or Firm*—Pyle & Piontek

[57] ABSTRACT

An apparatus for detailed and sharp self-viewing of the eye including the cornea or surface of the eye comprises a tube-like housing with a diffused light source at one end. The light source projects light through a pin-hole in the center of a baffle in the tube housing towards a convex lens near the other end of the tube housing. When a user holds the tube housing with the convex lens close to his eye, a sharp and detailed image of the eye is projected into the tube and may be viewed by the user. The device is particularly useful for self visual inspection of the condition of the eye cornea, for inspecting contact lenses for air bubbles or debris lying between the lens and the eye, and for inspecting the installation and condition of piggy back lenses.

20 Claims, 1 Drawing Sheet

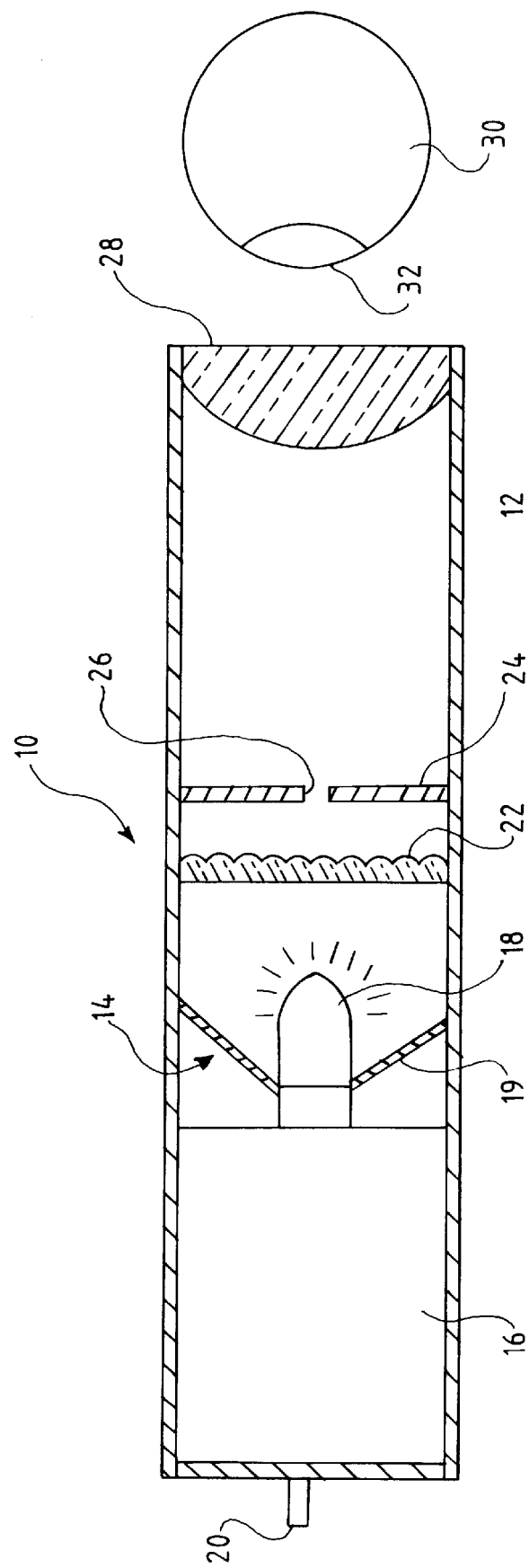

SELF-VIEWING DEVICE FOR EYES

FIELD OF THE INVENTION

This invention relates to a portable apparatus for self viewing of the eye.

BACKGROUND OF THE INVENTION

Self examination of the eye is useful for a number of purposes. Sufferers of diseases of the eye, for instance, may need to inspect the eye closely for indications of its condition. Also, users of contact lenses often encounter problems with debris or air bubbles between the lens and the eye, which can lead to irritation of the surface of the eye, pain, and potential permanent damage to the cornea. The kind of detailed self inspection of the eye required for these and many other purposes is presently impossible to accomplish alone.

Several diseases of the eye are indicated by the visual condition of the eye, such as glaucoma or keratoconus, for instance. People who suffer from these diseases may need to closely monitor the visual condition of the eye regularly. While it is possible of course to have one's eye condition checked by a doctor, for a variety of reasons it is not always convenient to visit a doctor at a frequency that may be required.

Also, for people who may not suffer such diseases but may simply wear contact lenses, an inspection of the eye can be most useful.

It is also most difficult, if not impossible, for an individual to self-inspect the installation on the eye of piggy back lens systems of my previous U.S. Pat. No. 5,434,630, herein incorporated by reference. In order to ensure that the two lenses of that invention are properly configured, a very close inspection of the eye surface is required that is not possible using only a mirror. The '630 invention may not be operable with air bubbles or foreign matter between lenses. Further, while it may at times be possible to see or feel that an air bubble or debris is present using a mirror or other means, it is most difficult or impossible to determine whether the bubble or debris lies between lenses or between the eye and the bottom lens. The consistent presence of such bubbles or debris over the long term can lead to permanent and painful damage to the eye.

Devices have been described which allow for the self examination of the eye. These devices, however, may not prove useful for inspecting the eye to look for air bubbles or debris under a contact lens.

U.S. Pat. No. 3,787,112, for instance, discloses a method and apparatus for ocular self examination. The device claimed and described introduces non-collimated light into the eye. A chart is then viewed, with the user seeing shadows on the chart corresponding to any damage on the retina, tumors, or scar tissue. The device of the '112 patent does not reflect an image of the eye itself, and therefor does not allow for an inspection of the actual eye surface. It instead shines light into the eye and provides a magnified chart to be read. Things such as air bubbles under a contact lens may not be detecatable with this device. For these reasons, the device of the '112 patent is of little use in detecting materials such as air bubbles under a contact lens. Further, the device and method disclosed relate to a large, bulky apparatus that does not lend itself to portability.

U.S. Pat. No. 3,903,870 also describes a method and device for ocular self examination. The '870 device utilizes a point source of light placed at the anterior focus of the eye. Because this point source is located at the anterior focus of the eye, light beams from it will be reflected and collimated from the rear surface of the eye, the retina. This will in turn cause an image of the retina to be reflected outward. The user may thereby inspect the image and compare it to images of healthy retinas to discern any differences and thus be alerted to potential problems. The '870 device is thus not particularly useful to detect such things as debris under a contact lens, or a damaged or inflamed cornea. Also, as the '870 device uses only a point light source and not a lens, the observed image may not be magnified to an extent required to observe with sufficient detail the eye, particularly for users with limited vision.

Neither the invention of the '870 patent nor that of the '112 patent, nor similar devices, would be useful for using the subject of my previous U.S. Pat. No. 5,434,630. The '870 device or the '112 device would not be able to adequately indicate the orientation of the piggy-backed lenses on the eye surface as is required to properly use the subject of my '630 patent.

An unresolved need therefor exists for an easy to use device for the self visual inspection of the condition of the eye.

OBJECTS OF THE INVENTION

It is an object of the invention to provide an apparatus for the self inspection of the eye.

It is a further object of the invention to provide a compact, easily transportable apparatus for the self inspection of the eye.

It is further object of the invention to provide a method for self inspecting the eye.

SUMMARY OF THE INVENTION

The present invention comprises a self viewing device for the eyes, as well as a method for self inspection of the eye.

In the preferred embodiment of the apparatus of the invention, a tube is provided with a source of diffused light at one end. The light source may comprise a bulb and an electrical supply such as a battery. To provide diffused light, the bulb may be coated or a diffusing disk may be located inwardly from the bulb. Inwardly of the diffused light source is an opaque disk with a small pinhole opening near its center.

At the other end of the tube is located a focusing lens, spaced from the pinhole opening. When the light source is activated, the user can hold the lens end close to the open eye, and a detailed, magnified image of the eye surface, cornea, and illuminated lens (or pupil) is projected into the tube for viewing with the same eye. The eye lens appears illuminated, so that debris on the eye surface over the otherwise darkened eye lens is easily detected. In addition to debris, the condition of the cornea and eye lens as well as the presence of air bubbles under or a tear in a contact lens may thereby be detected. The image displayed is magnified by a factor of several times, with the degree of magnification easily controlled by moving the device closer or farther from the eye. The magnification factor is at least 2, and can be over 5 to 10.

Also, the eye viewing device of the present invention is very useful for using the piggy back lens system of my previous U.S. Pat. No. 5,434,630. Use of the present invention allows wearers of the piggy back lenses to determine whether air bubbles or debris are present, and if so whether the material is located between lenses or between the lens and the eye. Such matter may be trapped and unable to work itself free, and should it remain undetected it could cause permanent eye damage. No prior art device has proven useful for such an application.

The device of the present invention is also particularly well suited for inspecting damage to the eye and the condition of its viewable parts in relation to eye diseases such as keratoconus or glaucoma. Sufferers of these diseases may use the device to regularly and quickly monitor the condition of the eye. A change in condition, such as an elevation in the ocular pressure, is readily detected using the apparatus of the invention.

Users who don't wear contact lenses or suffer from eye illnesses can use the apparatus of the invention to inspect the eye for purposes as simple as determining whether an eyelash or other debris is present. Also, because the viewed image appears magnified by the order of several times, the apparatus of the invention is very useful for users with limited vision.

Also, a preferred embodiment of the device of the invention is compact, lightweight, and easily transportable. The compact embodiment of the invention has approximately the dimensions of a pen-light, with a length of or less than about 6 inches, a diameter of or less than about ½ inches, and a weight of less than 2 ounces. It thus lends itself well to being carried about by a user, fitting conveniently in a shirt pocket or purse, for frequent use.

The present invention further comprises a method for self viewing the eye, preferably comprising the steps of passing light through a housing having an opaque baffle with a pinhole at its center, passing the light from said pinhole through a convex lens near the housing end, and reflecting the light from the convex lens off of the eye to create a reflected, magnified image of the eye in the housing. The eye lens appears to be illuminated, providing a bright background against which debris, air bubbles, or contact lens faults which may be on the surface of the eye will be clearly visible. Using the method of the invention a user may easily and readily observe the eye, as generally discussed above.

The above brief description sets forth rather broadly the more important features of the present disclosure so that the detailed description that follows may be better understood, and so that the present contributions to the art may be better appreciated. There are, of course, additional features of the disclosure that will be described hereinafter which will form the subject matter of the claims appended hereto. In this respect, before explaining embodiments of the disclosure in detail, it is to be understood that the disclosure is not limited in its application to the details of the construction and the arrangements set forth in the following description or illustrated in the drawings. The present invention is capable of other embodiments and of being practiced and carried out in various ways, as will be appreciated by those skilled in the art. Also, it is to be understood that the phraseology and terminology employed herein are for description and not limitation.

The objects of the invention have been well satisfied. These advantages and others will become more fully apparent from the following detailed description when read in conjunction with the accompanying drawings.

BRIEF DESCRIPTION OF THE DRAWINGS

FIG. 1 is a side view, partly in cross section, of a preferred embodiment of the apparatus of the present invention.

DESCRIPTION OF THE PREFERRED EMBODIMENTS

Turning now to the drawing, FIG. 1 shows a preferred embodiment of the apparatus of the invention. Tube 10 has an interior wall 12. One end of the tube may be closed and contains a light source 14, such as a conventional flashlight comprising a battery 16, preferably a single type AAA battery, electrically connected to bulb 18 with reflector 19, and switch 20 for turning the bulb on and off. In order to prevent images associated with the light source 14 from being projected into tube 10, a means for diffusing the light is included. This may comprise, for example, a frosted coating on the surface of bulb 18, or a preferred diffusing element 22 located in the tube inwardly from the bulb. Element 22 may take the form of a paper thin plastic sheet having a limited amount of pigment therein, such as a milky white plastic disc.

The light source 14 may be self-contained within the tube 10 for the sake of convenience. Any external source of light of good intensity may also be employed. The interior wall 12 of the tube 10 is preferably rendered non-reflective, for example, by applying a black coating to the interior surface.

Located closely adjacent light source 14 is an opaque baffle or disk 24, which is preferably sealed within the tube and prevents passage of light except through small pinhole passage 26 located in the center of the disk. Preferably, the diameter of pinhole passage 26 is from about 100 to about 300 microns.

Located at the other end of the tube is convex lens 28 having a focal length of from about 20 to about 30 mm. Lens 28 is preferably achromatic, and is held closely adjacent to eye 30 to view an image or virtual image of the eye 30 within the tube. The image produced using the preferred achromatic lens has been found to be sharper and clearer than images from non-achromatic lenses. Lens 28 may be oriented with convex side inwards or outwards of the housing, without apparent effect on the resultant image. The distance between pinhole passage 26 and lens 28 is of the order of 2.5 to 3.5 inches. The diameter of the thin wall tube is about 0.5 to about 0.75 inches, and the overall length of the device, depending on the nature of the light source, may be of the order of six to nine inches.

When the preferred device is illuminated with light passing through pinhole passage 26 and lens 28 closely adjacent to eye 30, a clear, highly detailed, magnified, non-inverted image of eye 30 becomes available, including a detailed image of eye 30 cornea 32. The image appears to reside within the tube between pinhole passage 26 and lens 28, and appears to be of the cornea against an illuminated lens background. While the precise manner by which the apparatus of the invention functions is not clearly understood, it is apparent that light is being reflected from the eye back through the lens, although the device itself does not employ a reflective surface or a mirror. Also, the image is not inverted and corresponds to the actual image of the eye and cornea. The eye lens, or pupil, appears illuminated, so that debris or air bubbles residing in front of the illuminated pupil are clearly visible. Because the pupil is otherwise dark, these materials could not easily otherwise be detected with use of a mirror, for instance.

The viewed image is also magnified; although the exact magnification is not exactly known, it is at least a factor of several times. The degree of magnification may be easily controlled by moving the device closer or farther from the eye. The device need not be located at the anterior focus of the eye to operate properly. Suprisingly, no loss of sharpness of focus results when enlarging or making smaller the displayed image by moving the device closer or farther from the eye.

The device of the invention may further comprise a preferred, compact embodiment suitable for portable use.

This preferred compact embodiment will have the elements as described above and generally shown in FIG. 1; it is noted however that FIG. 1 is not drawn to scale. In this embodiment, the device has the approximate size and weight of a penlight, with a length of or less than about 6 inches, and a diameter of or less than about ½ inches.

The design of the present invention allows for light of sufficient intensity to be generated using only a single small, lightweight standard type AAA battery for an overall apparatus lightweight. In particular, it is believed that the presence of lens 28 with its resultant light and image magnification allows for a lower power light source to be used than is possible in devices of the prior art. In addition, the effect of lens 28 in magnifying the reflected image of the eye allows for small device components to be used. The housing may be constructed of aluminum, further enabling a lightweight embodiment. In fact, a weight of less than about 2 ounces may be achieved. The on-off switch in such compact embodiments may comprise a rotatable portion of the tube housing, so that accidental powering on is made difficult while carrying the device in a pocket or a purse. Still more compact and lightweight embodiments are also within the scope of the invention, such as may be possible with alternate, lighter weight and more compact batteries.

A preferred method of the invention comprises passing light through a housing having an opaque baffle with a pinhole of 100–300 micron diameter near its center, through an achromatic convex lens with a focal length of 20–30 mm near the housing end, and finally reflecting the light from a user's eye back through the convex lens to create an image of the eye that appears to be in the housing. Preferably, the pinhole and lens are spaced from one another by a distance of about 2.5 to 3.5 inches, and the light transmitted is diffused. The light may be made diffused by passing it through a diffuser in the housing before passing through the pinhole.

While preferred embodiments and example configurations have been shown and described, it is to be understood that various further modifications and additional configurations will be apparent to those skilled in the art. It is intended that the specific embodiments and configurations disclosed herein are illustrative of the preferred and best modes for practicing the invention, and should not be interpreted as limitations on the scope of the invention as defined by the appended claims.

What is claimed is:

1. A reflective self viewing device for the eye, said device comprising:
    a) a housing having a first end and a second end;
    b) an opaque baffle in said housing near said first end having a central pinhole;
    c) a convex lens at said housing second end; and
    d) a source of diffused light located outwardly from said pinhole for causing light to pass through said pinhole toward said lens, with said lens able to be positioned closely adjacent to the eye for directing said light onto the eye and said light reflecting back from the eye and thereby reflecting an image of the eye appearing for self viewing.

2. The device of claim 1 wherein said lens has a focal length of about 20 to about 30 mm.

3. The device of claim 2 wherein said lens is an achromatic lens.

4. The device of claim 1 wherein said pinhole has a diameter of from about 100 to about 300 microns.

5. The device of claim 1 wherein said pinhole and said lens are spaced from about 2.5 to 3.5 inches from one another.

6. The device of claim 1 wherein said source of light comprises a diffuser located between said source of light and said opaque baffle, and said light is diffused.

7. The device of claim 1 wherein said source of light comprises a battery connected to a light bulb contained within said tube first end.

8. The device of claim 7, wherein said battery comprises a single type AAA battery.

9. The device of claim 1 wherein said housing is tubular shaped.

10. The device of claim 9, wherein said housing has a length of no more than about 6 inches, and a diameter of no more than about ½ inches.

11. The device of claim 1 wherein said housing is comprised of aluminum.

12. The device of claim 1 wherein said image appears magnified, and is of the eye cornea against an illuminated eye lens background, and appears to reside in said housing.

13. The device of claim 1, wherein said device has a weight of less than about 2 ounces.

14. A reflective self viewing device for the eye surface, said device comprising:
    a) a substantially tubular housing having a first end and a second end, having a length of no more than about 6 inches, and a diameter of no more than about ½ inches;
    b) an opaque baffle in said housing near said first end having a central pinhole, said pinhole diameter between approximately 100 to 300 microns;
    c) a convex lens having a focal length of between approximately 20 mm and 30 mm at said housing second end spaced approximately 2.5 to 3.5 inches from said baffle; and
    d) a lightbulb connected to a single battery and a diffuser located outwardly from said pinhole for causing diffused light to pass through said pinhole toward said lens, with said lens able to be positioned closely adjacent to the eye for directing said light onto the eye and said light reflecting back from the eye, with a reflected magnified image of the cornea thereby appearing in said housing for self viewing.

15. A method of self examining the eye comprising the steps of:
    a) passing light through a housing having an opaque baffle with a pinhole at its center;
    b) passing said light from said pinhole through a convex lens near said housing end;
    c) reflecting said light from said convex lens off of the eye to create a reflected image of the eye in said housing.

16. The method of claim 15 wherein said convex lens has a focal length of about 20 to about 30 mm.

17. The method of claim 15 wherein said convex lens is an achromatic lens.

18. The method of claim 15 wherein the diameter of said pinhole is from about 100 to about 300 microns, and said pinhole and said lens are spaced from about 2.5 to 3.5 inches from one another.

19. The method of claim 15 wherein said light is diffused light and is produced by passing light through a diffuser before passing through said opaque baffle.

20. The method of claim 15 wherein said reflected image is of the cornea against an illuminated eye lens background.

* * * * *